(12) United States Patent
Tatarczyk et al.

(10) Patent No.: US 8,625,092 B2
(45) Date of Patent: Jan. 7, 2014

(54) APPARATUS FOR MEASURING A SPECTRAL DISTRIBUTION OF A TRANSLUCENT PRINTED PRODUCT PRODUCED WITH A PRINTING DEVICE

(75) Inventors: Christina Tatarczyk, Grobenzell (DE); Joachim Tatarczyk, Grobenzell (DE)

(73) Assignee: Theta System Elektronik GmbH (DE)

( * ) Notice: Subject to any disclaimer, the term of this patent is extended or adjusted under 35 U.S.C. 154(b) by 546 days.

(21) Appl. No.: 12/555,046

(22) Filed: Sep. 8, 2009

(65) Prior Publication Data

US 2010/0066999 A1    Mar. 18, 2010

(30) Foreign Application Priority Data

Sep. 5, 2008    (DE) .................. 10 2008 045 987

(51) Int. Cl.
*G01J 3/28*    (2006.01)
(52) U.S. Cl.
USPC ........................................................ 356/328
(58) Field of Classification Search
USPC ............ 356/328, 429, 432, 239.1, 239.3, 326
See application file for complete search history.

(56) References Cited

U.S. PATENT DOCUMENTS

| | | | |
|---|---|---|---|
| 4,226,538 A * | 10/1980 | Van Beeck | 356/430 |
| 4,898,467 A | 2/1990 | Milch | |
| 5,034,616 A | 7/1991 | Bercovitz | |
| 5,506,656 A * | 4/1996 | Nitsch | 356/443 |
| 5,592,291 A * | 1/1997 | Iida | 356/326 |
| 6,548,812 B1 * | 4/2003 | Schumacher | 250/339.02 |
| 6,732,917 B1 | 5/2004 | Benz et al. | |
| 2007/0229822 A1 | 10/2007 | Tatarczyk et al. | |

FOREIGN PATENT DOCUMENTS

| | | |
|---|---|---|
| DE | 102006015375 | 10/2007 |
| EP | 0395833 A1 | 1/1990 |

* cited by examiner

*Primary Examiner* — Kara E Geisel
(74) *Attorney, Agent, or Firm* — Gerald E. Hespos; Michael J. Porco; Matthew T. Hespos

(57) ABSTRACT

An apparatus (10) measures a spectral distribution of a translucent printed product (12) produced with a printing device. The apparatus (10) has an illuminating source (20) for illuminating the printed product (12), an optoelectronic measuring means (32) for measurer the transmittance value of a section of the spectrum of the light (26) transmitted through the printed product (12), an optical disperser (28) for dispersing the wavelengths of the transmitted light (26), and a light entry gap plane that is definitive for the disperser (28). The light entry gap plane that is definitive for the disperser (28) is created by the surface of the printed product (12) to be examined.

14 Claims, 2 Drawing Sheets

ABSTRACT FOR MEASURING A SPECTRAL
DISTRIBUTION OF A TRANSLUCENT
PRINTED PRODUCT PRODUCED WITH A
PRINTING DEVICE

BACKGROUND OF THE INVENTION

1. Field of the Invention

The invention relates to an apparatus for measuring a spectral distribution of a translucent printed product produced with a printing device, which comprises an illumination means for illuminating the printed product, an optoelectronic measuring means for measuring the transmittance value of at least one section of the spectrum of the light transmitted trough the printed product, an optical dispersing means for dispersing the wavelengths of the transmitted light, and a light entry gap plane that is definitive for the dispersing means.

2. Description of the Related Art

Various types of quality monitoring and control of printing processes are known in the graphics industry. One of the measuring methods used in this case is color measurement by means of an analysis of the spectral distribution of the light reflected from a printed product. Known are measuring systems for a spectral measurement of translucent printed products which measure individual measuring positions.

From DE 10 2006 015 375.8-52 an apparatus is known for measuring a spectral distribution of the reflectance value of a section of a printed product produced with a printing device. Apparatus which measure spectrally resolve the spectrum of the reflected light in bandwidths of, for example, 20 or fewer nanometers and use these to determine the associated reflectance values. From the reflectance values, various characteristic color values can subsequently be derived.

The invention is based on the object of configuring an apparatus for measuring a spectral distribution of a section of a printed product produced with a translucent printing device more economically and more compactly with the same or improved measurement quality.

SUMMARY OF THE INVENTION

According to the invention, an apparatus for measuring a spectral distribution of a translucent printed product produced with a printing device comprises an illumination means for illuminating the printed product, an optoelectronic measuring means for measuring transmittance values of a section of the spectrum of the light transmitted through the printed product, an optical dispersing means for dispensing the wavelengths of the transmitted light and a light entry gap plane that is definitive for the dispersing means, wherein the light entry gap plane that is definitive for the dispersing means is created by the surface of the translucent printed product to be examined.

The light entry gap plane that is definitive for the dispersing means is created by the surface of the translucent printed product to be examined, while the printed product to be examined is linear irradiated from the back. Therefore, with the solution according to the invention, an apparatus which can be produced, mounted and even maintained particularly economically is provided. This is done in that the measuring means of an apparatus for measuring a spectral distribution has led to it a gap-like or linear light beam about 1 mm to about 2 mm wide, which is transmitted directly in this "gap form" through the surface of the printed product to be examined. The solution according to the invention can consequently dispense with complicated optics between the product and an entry gap of a spectroscope.

The invention is based, inter alia, on the finding that it is not necessary to illuminate the object to be examined over as large an area as possible and as homogeneously as possible but that point-like or locally limited illumination is considerably more practical if the region of the printed product which is illuminated to a limited extent is simultaneously used as an entry light beam for an apparatus according to the invention. In the apparatus, the entry light beam is subsequently diffracted, dispersed and broken down.

According to the invention, it is also possible to dispense with the entry gap or an entry gap aperture stop itself, specifically because the gap shape of the entry light beam that is definitive for the dispersing means is created by means of linear illumination of the printed product to be examined. The linear illumination can be created particularly advantageously by means of a cylindrical lens or optics and, if appropriate, an aperture stop in front of the illumination means. In this case, considerably lower requirements have to be placed on the quality and the accuracy of these optical elements comprising cylindrical optics and aperture stop than in the case of known optics, as are provided between a product to be measured and an entry gap of known spectroscopes.

The illumination means used for the apparatus according to the invention is particularly advantageously at least one light-emitting diode which, with low costs and little requirement for space, provides a large quantity of light. The plane of the illuminating light beam directed from the illumination means onto the product to be measured is advantageously directed at an angle of about 90° to the surface of the printed product and, also at an angle of about 180° to the viewing or observation direction of the measuring means. In this case, the viewing direction is simultaneously the direction of the gap-like light beam transmitted through the printing product to the dispersing means, which is then diffracted at this dispersing means.

Preferred as dispersing means according to the invention is a diffraction grating which, as mentioned at the beginning, permits a high resolution of the spectral distribution. The preferred grating is a transmission grating. Alternatively, a reflection grating can also be used. If necessary, prisms or characteristic filters can also be used but distinct preference given to the transmission grating because of the compact design of the apparatus according to the invention which can be achieved therewith.

The preference for a transmission grating is also based not least on the fact that, in the apparatus according to the invention, only one projection lens or optics is also preferably arranged between the measuring means and the dispersing means. According to the invention, on the other hand, complicated prism systems, as are provided in this region in the case of known spectroscopes, are deliberately omitted.

This omission is possible since, according to the invention, the measuring means used is in particular a sensor which has a large number of photoelements and can accordingly offer high resolution. The measuring means used is particularly preferably an inexpensive surface sensor, as is known from conventional digital cameras for image recordings.

The apparatus according to the invention can, moreover, be configured particularly compactly and without complex prism optics in the beam path by the arrangement formed from optoelectronic measuring means and optical dispersing means, and in particular also from the projection optics, being oriented in its longitudinal direction obliquely with respect to the direction of the light beam transmitted through the printed product and incident on the dispersing means. The arrangement is in particular advantageously set obliquely at an angle of between about 20° and about 40° to the direction of the light beam incident on the dispersing means.

To improve the apparatus according to the invention further with regard to its measuring accuracy, an aperture stop preferably is provided above the surface of the printed product for holding back external light transmitted through the printed product.

In the following text, an exemplary embodiment of an apparatus according to the invention will be explained in more detail by using the appended schematic drawings.

DETAILED DESCRIPTION OF THE PREFERRED EMBODIMENT

Figure 1:
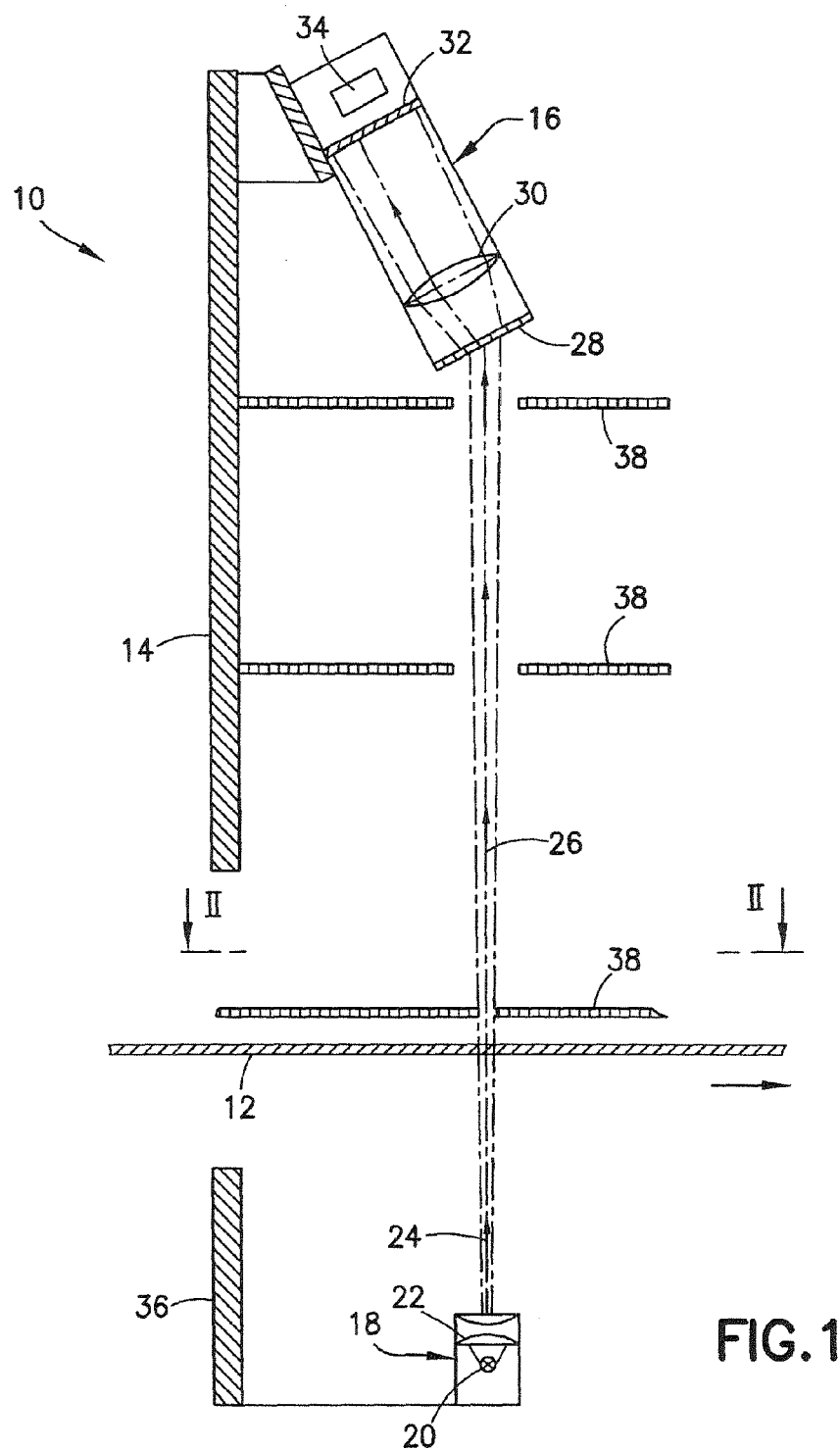
FIG. 1 shows a longitudinal section of an exemplary embodiment of an apparatus according to the invention for measuring a spectral distribution in transmission of a section of a translucent printed product produced with a printing device.
Figure 2:
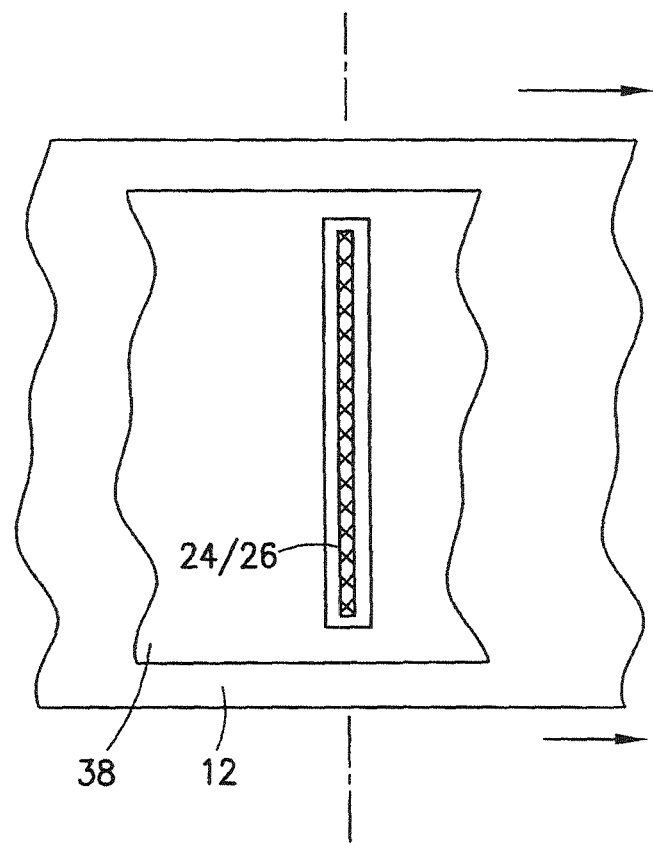
FIG. 2 is a section taken along line II-II in FIG. 1.

In the figures, an apparatus 10 for monitoring the quality of a flat translucent printed product 12 produced with a printing device, not shown further, is illustrated. The translucent printed product 12 is web-like and, in relation to the figures, is moved through under the apparatus 10 from left to right. On the translucent printed product 12 there are printed graphic figures, which are to be tested with regard to the quality of their printed image.

The apparatus comprises a rod-like holder 14 which is oriented substantially vertically and in whose upper end section a camera unit 16 is mounted and a rod-like holder 36 which is oriented substantially vertically and in whose lower end section an illuminating unit 18 is mounted.

The illuminating unit 18 comprises an illumination means 20 in the form of a light-emitting diode emitting white light, in front of which cylindrical optics 22 is arranged in the beam path. The cylindrical optics 22 focuses the light emitted by the light-emitting diode 20 to form a strip-like or gap-like illuminating light beam 24 which is about 1 mm to 2 mm wide and whose beam plane is directed at an angle of about 90° directly onto the surface of the translucent printed product 12 to be examined.

From the surface of the printed product 12 illuminated in a strip-like manner towards the back in this way, a likewise strip-like or gap-like light beam 26 is transmitted in the direction of the camera unit 16. The main radiation direction of the light beam 26 is in this case directed approximately at an angle of 90° to the surface or plane of the flat translucent printed product 12.

The light beam 26 strikes the camera unit 16 at a dispersing means 28 in the form of a diffraction grating. At this dispersing means 28, the spectrum of the light beam 26 transmitted through the printed product 12 is broken down and diffracted and, as a "fanned out" light beam 26, passes on further to a projection optics 30 arranged in the interior of the camera unit 16. Using this projection optics 30, the alignment of the transmitted and diffracted light beam 26 is corrected slightly in order that it covers as extensively as possible a measuring means 32 in the form of a rectangular surface sensor located behind the projection optics 30. In this case, the measuring means 32 is provided with a large number of individual photoelements, which are able to report the luminous intensity of the incident light individually to evaluation electronics 36 arranged behind the measuring means 32.

In this case, together with its dispersing means 28, its projection optics 30 and its measuring means 32, the camera unit 16 is placed obliquely at an angle of about 30° to the longitudinal direction of the transmitted light beam 26 in such a way that the light diffracted by the dispersing means 28 is projected onto the measuring means 32 over virtually the entire area without complicated optical correcting means, such as prisms.

To improve the measuring accuracy of the entire apparatus 10, around the illuminating light beam 24 and the transmitted light beam 26, at a suitable distance, a total of three aperture stops 38 are also arranged in a substantially parallel orientation with respect to the surface of the printed product 12, with which stops external light is kept away from the dispersing means 28 of the camera unit 16.

In conclusion, it should be noted that all the features which are cited in the application documents and in particular in the dependent claims, despite the formal references made to one or more specific claims, are also intended to be assigned individual protection individually or in any desired combination.

What is claimed is:

1. Apparatus (10) for measuring a spectral distribution of a translucent printed product (12) produced with a printing device and moved in a moving direction relative to the apparatus (10), comprising an illumination means (20) for producing a plane of light (26) aligned substantially normal to the printed product (12) and substantially normal to the moving direction for illuminating a substantially linear strip of the printed product (12), a camera unit (16) mounted fixedly on a side of the printed product (12) opposite the illumination means (20) and having an optical dispersing means (28) disposed to be impinged upon by the plane of light passing through the translucent printed product (12), the dispersing means (28) being oriented for dispersing the wavelengths of the transmitted light (26) outward from the plane of the light (26) and transmitting the dispersed light (26) of the light plane from the dispersing means (28) into the camera unit (16), a rectangular array of photo elements (32) disposed in the camera unit (16) at a position to be impinged upon by dispersed wavelengths of light transmitted by the dispersing means (28) and projection optics (30) between the array of photo elements (32) and the dispersing means (28) for correcting the dispersed light to achieve optimum coverage on the array of photo elements (32), the projection optics (30) being the single projection optics between the translucent printed product (12) and the array of photo elements (32), wherein the light (26) from plural locations along the illuminated strip of the printed product (12) is diffracted by the dispersing means (28) for examining the translucent printed product (12) along the illuminated strip.

2. Apparatus according to claim 1, wherein a shape of the transmitted light (26) directed to the dispersing means (28) is affected by a surface of the translucent printed product (12) to be examined.

3. Apparatus according to claim 2, wherein the illumination (20, 22, 24) of the printed product is configured by means of at least one light-emitting diode.

4. Apparatus according to claim 3, wherein only one projection optics (30) is arranged between the photo elements (32) and the dispersing means (28).

5. Apparatus according to claim 4, wherein the photo elements (32) are configured as a surface sensor.

6. Apparatus according to claim 3, wherein an aperture stop (38) for holding back external light transmitted through the printed product (12) is provided between the illumination means and the surface of the printed product (12).

7. Apparatus according to claim 6, wherein he printed product (12) is flat.

8. Apparatus according to claim 1, wherein the illumination (20, 22, 24) of the printed product (12) comprises at least one light-emitting diode.

9. Apparatus according to claim 1, wherein only one projection optics (30) is arranged between the photo elements (32) and the dispersing means (28).

10. Apparatus according to claim 1, wherein the photo elements (32) are configured as a surface sensor.

11. Apparatus according to claim 1, wherein an aperture stop (38) for holding back external light transmitted through the printed product (12) is provided between the illumination means and the surface of the printed product (12).

12. Apparatus according to claim 1, wherein the printed product (12) is flat.

13. Apparatus according to claim 1, wherein the optical dispersing means (28) comprises a diffraction grating having an array of parallel slits, the dispersing means (28) being disposed and oriented so that the slits of the diffraction grating are substantially parallel to the plane of the light (26).

14. Apparatus (10) for measuring a spectral distribution of a translucent printed product (12) produced with a printing device, comprising an illumination means (20) for producing a plane of light (26) aligned substantially normal to the printed product (12) for illuminating a substantially linear strip of the printed product (12), an optoelectronic measuring means on a side of the printed product (12) opposite the illumination means (20) and having a rectangular array of photo elements (32) for measuring the transmittance value of a section of the spectrum of the light (26) transmitted through the printed product (12), an optical dispersing means (28) between the printed product (12) and the photo elements (32), the dispersing means (28) being disposed and oriented for dispersing the wavelengths of the transmitted light (26) outward from the plane of the light (26) and transmitting the dispersed light (26) of the light plane from the dispersing means (28) toward the rectangular array of photo elements (32), wherein the light (26) from plural locations along the illuminated strip of the printed product (12) is diffracted by the dispersing means (28) for examining the translucent printed product (12) along the illuminated strip and wherein the optoelectronic measuring means, the dispersing means (28) and a projection optics (30) associated with the optoelectronic measuring means and the dispersing means (28) define an arrangement (16) that is arranged along a longitudinal direction oriented obliquely with respect to the direction of the plane of the light (26) transmitted through the printed product (12) and incident on the dispersing means.

* * * * *